US009423408B2

(12) United States Patent
Triva (10) Patent No.: US 9,423,408 B2
(45) Date of Patent: Aug. 23, 2016

(54) APPARATUS AND PROCESS FOR TREATING BIOLOGICAL, MICROBIOLOGICAL AND/OR CHEMICAL SAMPLES

(75) Inventor: Daniele Triva, Bovezzo (IT)

(73) Assignee: COPAN INFORMATION TECHNOLOGIES S.R.L., Brescia (IT)

( * ) Notice: Subject to any disclaimer, the term of this patent is extended or adjusted under 35 U.S.C. 154(b) by 166 days.

(21) Appl. No.: 14/113,741

(22) PCT Filed: May 2, 2012

(86) PCT No.: PCT/IB2012/052193
§ 371 (c)(1),
(2), (4) Date: Oct. 24, 2013

(87) PCT Pub. No.: WO2012/150555
PCT Pub. Date: Nov. 8, 2012

(65) Prior Publication Data
US 2014/0050361 A1  Feb. 20, 2014

(30) Foreign Application Priority Data

May 3, 2011 (IT) .............................. MI2011A0739

(51) Int. Cl.
*G06K 9/00* (2006.01)
*G01N 35/00* (2006.01)
*B01L 9/00* (2006.01)
*G01N 35/04* (2006.01)

(52) U.S. Cl.
CPC ................ *G01N 35/00* (2013.01); *B01L 9/523* (2013.01); *B01L 2300/022* (2013.01); *B01L 2300/027* (2013.01); *B01L 2300/0829* (2013.01); *G01N 2035/0491* (2013.01)

(58) Field of Classification Search
None
See application file for complete search history.

(56) References Cited

U.S. PATENT DOCUMENTS

| 6,790,636 | B1 | 9/2004 | Star et al. |
|---|---|---|---|
| 2004/0092025 | A1 | 5/2004 | Mordekhay |
| 2004/0224370 | A1 | 11/2004 | Jiang et al. |
| 2004/0241044 | A1 | 12/2004 | Mordekhay |
| 2005/0042692 | A1 | 2/2005 | Star et al. |
| 2005/0102056 | A1 | 5/2005 | Du |
| 2006/0012773 | A1 | 1/2006 | Schutze et al. |
| 2006/0188406 | A1 | 8/2006 | Frost, III |
| 2007/0072168 | A1* | 3/2007 | Ryle .................................. 435/4 |
| 2008/0042839 | A1 | 2/2008 | Grater et al. |
| 2010/0078293 | A1 | 4/2010 | Yamanaka et al. |
| 2012/0001729 | A1 | 1/2012 | Goncalves Guedes |

FOREIGN PATENT DOCUMENTS

| DE | 198 38 232 A1 | 3/2000 |
|---|---|---|
| DE | 20 2004 020 510 U1 | 9/2005 |

(Continued)

*Primary Examiner* — Stephen R Koziol
*Assistant Examiner* — Amandeep Saini
(74) *Attorney, Agent, or Firm* — Pearne & Gordon LLP (57) ABSTRACT

A process for treating samples of biological, microbiological and/or chemical material, comprising at least a step of arranging a plurality of samples of biological, microbiological and/or chemical material on a corresponding plurality of housing seats (4) of a transportable support body (3) of a support device (2), further comprising a step of projecting (3) onto the support body (3) at least a light signal (18), during the step of arranging the plurality of material samples, at the effective position or housing seat or seats (4) wherein each sample of material is arranged, such as to guide the positioning or to indicate the positioning visibly.

35 Claims, 7 Drawing Sheets

(56) References Cited

FOREIGN PATENT DOCUMENTS

| DE | 20 2005 017 946 U1 | 1/2006 |
| EP | 1048723 A1 | 11/2000 |
| WO | 2004/044175 A2 | 5/2004 |
| WO | 2004/045768 A1 | 6/2004 |
| WO | 2005/026692 A2 | 3/2005 |
| WO | 2005/098455 A1 | 10/2005 |
| WO | 2010/116216 A1 | 10/2010 |
| WO | 2012/150555 A1 | 11/2012 |

* cited by examiner

APPARATUS AND PROCESS FOR TREATING BIOLOGICAL, MICROBIOLOGICAL AND/OR CHEMICAL SAMPLES

The present invention relates to an apparatus and a process for treating samples or analytes of biological, microbiological and/or chemical material.

The invention further relates to a support device for samples of biological, microbiological and/or chemical material, an interface device with the support device and a use of the devices.

The invention is particularly applicable in the sanitary, clinical, environmental, chemical and industrial field, as well as in all cases in which a transportable or target support device is used, for example a metal (typically steel), glass or plastic plate, provided with a plurality of housing seats, in which samples of biological, microbiological, of biological, bacteriological, virological, chemical origin etc. can be inoculated (or sowed) or positioned for subjecting to subsequent analysis.

The invention can be applied, for example, with plates having a matrix arrangement of the housing seats and the known plates used for mass spectrometry examinations, such as: MALDI (Matrix-Assisted Laser Desorption/Ionization) or MALDI-TOF (Time of Flight), Petri dishes, supports for antibiograms, food testing, environmental analysis, etc.

The prior art comprises use of various types of support device or target, such as those mentioned above, having a support surface provided with a plurality of seats on which, by means of traditional methods, samples of material of biological, bacteriological, virological, chemical origin etc. are inoculated or deposited.

The seats of the support devices can be fashioned on the surface of the support devices by deformation thereof (for example by incision), or can simply be visually delimited using a border which bounds each seat, or can be undetectably undefined before use in the support devices, and therefore be simply constituted by positions on the support surface (identifiable only by specific coordinates in terms of abscissas and ordinates) which are in no way bounded or predefined before depositing of the sample and are only defined by inoculation and depositing of the sample.

The samples deposited on the support device are then subjected to specific examination processes or analyses which enable determination of some specific properties of the samples. For example, in the case of MALDI-TOF plates for mass spectrometry, the samples or analytes are first placed in a solution in a substance, called a matrix, for example organic (such as glycerol, picolinic acid, succinic acid, caffeic acid, etc.) and then deposited in a determined position on the support device, and then placed in a vacuum. A laser pulse extracts the molecular ions from the target or the support device, which ions, accelerated by an electric field, cross a flow tube and enable, after suitable calibration, determination of accurate information on the structure and molecular weight of the analytes.

For example, support devices are known that in general exhibit a matrix structure, with a plurality of seats arranged on the support body of the device in an ordered way, in rows and columns. Each sample, relative to a determined type of material having a determined origin (for example a specific patient or a sampling place) is then inoculated or deposited on the support device in a precise position or seat, then to be subjected to laboratory examinations of an analytic or diagnostic type.

In all above-described cases, it is of fundamental importance that a trace is kept of the exact positioning of each sample on the support device, such as to be able correctly to match the results of the analyses performed on each sample with the correct origin thereof. An error in positioning of the samples on the support device and/or in matching the results of the analyses with the patients or origins of the samples can lead to serious consequences, as it leads to mismatching the results of the analyses and therefore produces errors of grave importance for the patients involved in the examinations. These errors would lead to switching pathologies for patients, or might give the wrong origins for the examinations carried out, leading to very serious risks for the health and indeed the lives of the people involved.

In order to reduce these risks, control patterns are predisposed, which in general are prepared before depositing the samples on the targets, in which various information relating to each sample is entered, for example the nature and origin of the sample, and in which the order or distribution pattern of the samples on the target or support device are decided. The operators who deposit the samples on the target must therefore refer to the control patterns and scrupulously follow the indications in order to prevent error. Also known are information systems and software programs that aid the operators in preparing the control patterns, which are however still manually compiled by the personnel involved, and which enable the printing of the control patterns for the use of the specialised personnel carrying out the positioning of the samples.

Alternatively the operators can simply deposit the samples in progressive order and consequently compile the control patterns, reporting what has been carried out. In any case, after the carrying out of the planned analysis of the samples, the results of the analysis are associated to the various patients or the origins of the samples according to the established order of the control patterns.

The present Applicant has found that the known solutions as described above lead to considerable drawbacks. In particular, the above-described procedures are considerably exposed to the risk of human error both during the compilation of the control patterns and during the depositing process of the samples on the support devices, and also during the following step of matching the analysis results to the origins of the samples.

Indeed, notwithstanding the experience of the operators, the use of management software, and the drawing-up of the control patterns, it is however still possible that an operator can commit an error in one of the cited steps, and thus the above-described solutions are intrinsically not secure and potentially subject to serious risks for the patients and persons involved in the analysis.

It is also possible that, during the step of depositing under a laminar flow hood, the specialised technician might need to vary the type and quantity of sample and the relative depositing thereof, in effect modifying the predetermined work pattern. This variation is identified by modifying the work pattern as written down on paper, verbally or by a change in a spreadsheet, thus remaining particularly subject to any eventual errors in interpretation and/or recording, and furthermore no information is kept regarding the traceability of the samples and the consequent variations in the work planning. Further, the above-described solutions are often complex, laborious and require very specialised and careful personnel.

Also, the above-described methods do not enable a sufficient degree of traceability of the whole process carried out, and the history of the analyses performed, the devices used and the persons involved; thus a source of potentially very important information—as far as specific contexts are concerned—is lost.

The main aim of the present invention is to obviate one or more of the problems encountered in the prior art.

An aim of the present invention is to provide an apparatus and a process for treating samples or analytes of biological, microbiological and/or chemical material, which enable eliminating or at least significantly reducing the risk of human error in the performing of the analytic processes and/or in determining the results thereof.

A further aim of the present invention is to provide an apparatus and a process for treating samples or analytes which exhibit a high degree of reliability and repeatability of the results.

A further aim of the present invention is to provide an apparatus and a process for treating samples or analytes which are extremely flexible and suitable for various operating needs and various types of analysis.

A further aim of the present invention is to provide an apparatus and a process for treating samples or analytes which enable simplification and an acceleration of the treatment processes of the information relating to the analyses of the samples.

A further aim of the present invention is to provide an apparatus and a process for treating samples or analytes which offer a high degree of traceability of the historical information relating to the analyses carried out and the devices and subjects involved, in order to enable further studies and provide further statistics on the results themselves.

A further aim of the present invention is to provide an apparatus and a process for treating samples or analytes which enable significantly increasing the security of the analytic processes of the samples or analyses, the security of the patients and in general the various subjects involved in the analyses.

A further aim of the present invention is to provide an apparatus and a process for treating samples or analytes which are simple to realise and which do not incur high costs.

These aims and others besides, which will more clearly emerge from the following description, are substantially attained by an apparatus and a process for treating samples or analytes, as well as a support device for samples of biological, microbiological and/or chemical material and by an interface device with the support device, according to what is expressed in one or more of the appended claims, taken alone or in combination, or in any combination with one or more of the further aspects described in the following.

In a further aspect, the invention further relates to a support device for samples of biological, microbiological and/or chemical material, comprising at least: a transportable support body (3) provided with a plurality of housing seats (4) suitable for each receiving at least a sample of biological, microbiological and/or chemical material; and an electronic memorising device (5), registrable and suitable for memorising a plurality of data relating at least to said samples of material and to the specific arrangement of each of said samples of material on said support body (3), in correspondence of each of the housing seats, said memorising device (5) being constrained to said support body (3) such as to be transportable together with the support body.

In a further aspect, the invention further relates to a support device, according to any one of the appended device claims, or the further aspects here indicated, wherein the memorising device (5) is cancellable and rewritable a plurality of times such as to enable selective cancellation and rewriting of the plurality of data and/or wherein the memorising device (5) is further provided with at least a univocal and sole identifying datum of the support device (2) and/or of at least a datum relating to a technical characteristic of the support device, selected at least from: a type of support, a type of surface of the support, a number of housing seats of the support, a positioning of the housing seats on the support, arrangement of the housing seats on the support, the coordinates of the housing seats on the support, a presence or not of culture media on the support and/or in that the memorising device (5) comprises at least a portion of non-rewritable memory in which the at least a univocal and sole identifying datum of the support device (2) and/or the at least a datum relating to a technical characteristic of the support device are permanently stored, and/or the at least a datum relating to a technical characteristic of the support device and/or wherein the memorising device (5) comprises at least a TAG or a registrable RFID transponder, provided at least with an electronic chip for memorising and an RFID antenna and/or wherein the memorising device (5) is a TAG or an RFID transponder of a passive type and/or wherein the memorising device (5) is integrated in the support body (3) and/or integrated internally of the support body (3) and/or wherein the support body (3) exhibits a flat, continuous and non-porous surface at and in proximity of the mounting point of the memorising device (5) on the support body (3).

In a further aspect, the invention further relates to an interface device (6) for interfacing with a support device (2), the interface device (6) comprising at least a support portion (7) suitable for housing the support device (2) and at least a transmitting device (8) suitable for reading and modifying contents of an electronic memorising device (5) of the support device (2) and/or comprises at least an RFID transceiver provided with at least an antenna for reading and/or writing the contents of the RFID-type electronic memorisation device.

In a further aspect, the invention further relates to an apparatus for treating samples of biological microbiological and/or chemical material, comprising at least a support device according to one or more of the above-indicated aspects, at least an interface device according to the indicated aspects, at least a processor (9) operatively connected to the interface device (6) and at least a software program (10) memorised on the processor (9) and suitable for managing the functioning of the interface device (6) and/or further comprising at least a visual signalling device (11) suitable for emitting a light signal (18) on a support body (3) of a support device (2) housed on the interface device (6), such as to visually indicate an effective housing position or seat (4) in which a sample of material is positioned, such as to guide positioning of the sample of material or such as to visually indicate the positioning or such as to define and delimit the plurality of housing seats on the support body and/or further comprising at least a registration device (12) of images or photographs such as to register images of at least the support body (3) during positioning of a plurality of samples of material and/or wherein the registration device is connected to the computer (9) in such a way as to transfer the images to the computer (9), which is destined to conserve and/or verify the images to confirm a real positioning of the plurality of samples of material on the support body (3).

In a further aspect, the invention further relates to a use of a support device (2) and/or of an interface device (6) according to one or more of the indicated aspects, for depositing, inoculation, transport and/or analysis of samples of biological, microbiological and/or chemical material in a diagnostic, medical, analytical, chemical, environmental, food and/or industrial field, and/or for performing such operations under a laminar flow hood.

In a further aspect, the invention further relates to a process for treating samples of biological, microbiological and/or chemical material, comprising at least a step of arranging a plurality of samples of biological, microbiological and/or chemical material on a corresponding plurality of housing seats (4) of a transportable support body (3) of a support device (2); and further comprising at least a step of following steps: memorising, on an electronic memorising device (5) constrained to the support body (3) such as to be transportable together with the support body (3), a plurality of data relating at least to the samples of biological, microbiological and/or chemical material and to a specific positioning of the samples on the support body (3), at the housing seats (4) and/or reading, from the electronic memorising device (5), constrained to the support body (3) such as to be transportable together with the support body (3), at least a univocal and sole identifying datum of the support device (2) and/or a plurality of data relating at least to the samples of biological, microbiological and/or chemical material and to a specific positioning to be performed for each thereof on said support body (3), in correspondence of said housing seats (4).

In a further aspect, the invention further relates to a support device, according to any one of the accompanying device claims, or the further aspects indicated herein, wherein a plurality of data memorised on a memorising device comprises, for each sample, at least a datum relating to a nature or type of the sample and/or the origin of the sample and at least a datum relating to the specific position of the sample on the support body of the support device to the specific housing seat in which the sample is arranged on the support body or at least a datum relating to instructions of the depositing procedure of samples on the support.

In a further aspect thereof, the invention further relates to a support device, according to any one of the accompanying device claims, or the further aspects indicated herein, wherein the support body comprises a first half-body in which the housing seats are defined and a second half-body in which the memorising device is housed, the first and the second half-bodies being reciprocally constrained such as to define the support device.

In a further aspect, the invention further relates to a support device, according to any one of the accompanying device claims, or the further aspects indicated herein, wherein the support body is made of a metal material, for example steel, and/or of a type re-usable a plurality of times or wherein the support body is realised in plastic material and/or wherein it is of a single-use disposable type.

In a further aspect thereof, the invention further relates to a support device, according to any one of the accompanying device claims, or the further aspects indicated herein, characterised in that it has a matrix arrangement of housing seats and/or wherein the seats are arranged according to an ordered positioning on the support body, for example a plurality of rows and columns, in a beehive arrangement, according to concentric circumferences or according to another ordered arrangement.

In a further aspect thereof, the invention further relates to a support device, according to any one of the accompanying device claims, or the further aspects indicated herein, wherein the support body is a support plate, for example a Petrie dish or a MALDI TOF mass spectrometry plate.

In a further aspect thereof, the invention further relates to a support device, according to any one of the accompanying device claims, or the further aspects indicated herein, wherein the support body is provided with at least a culture medium for micro-organisms at least at some of the housing seats.

In a further aspect thereof, the invention further relates to a support device, according to any one of the accompanying device claims, or the further aspects indicated herein, wherein the housing seats are defined and delimited in a finite number on the support body.

In a further aspect thereof, the invention further relates to a support device, according to any one of the accompanying device claims, or the further aspects indicated herein, wherein the seats are constituted by small wells fashioned on the body of the support for housing samples of biological, microbiological and/or or chemical materials.

In a further aspect thereof, the invention further relates to a support device, according to any one of the accompanying device claims, or the further aspects indicated herein, wherein the support device and/or an interface device with the support device are suitable and configured such as to be positioned and to operate in a protected environment in a laminar flow hood and to interface reciprocally in the protected environment.

In a further aspect thereof, the invention further relates to an apparatus, according to any one of the appended process claims, or the further aspects indicated herein, further comprising an automatic depositing device of the samples, operatively connected to the processor and/or commanded by the software program such as to inoculate (or sow) or deposit, guidedly, the samples in a plurality of housing seats on a support device.

In a further aspect thereof, the invention further relates to a process, according to any one of the appended process claims, or the further aspects indicated herein, wherein during a step of reading, by the electronic memorising device, constrained to the support body such as to be transportable together with the support body, at least a univocal and sole identifying datum of the support device and/or at least a datum relating to technical characteristics of the support device, selected from among the following: the type of support, the type of surface of the support, the number of housing seats of the support, the positioning of the housing seats on the support, the coordinates of the housing seats on the support, the presence or not of culture media on the support.

In a further aspect thereof, the invention further relates to a process, according to any one of the appended process claims, or the further aspects indicated herein, further comprising a step of using a univocal and sole identifying datum of the support device and/or one or more articles of data relating to technical characteristics of the support device, read by the electronic memorising device, in a software program suitable for managing a functioning of an interface device and/or in a software program suitable for visualising a representation of the support device and the relative arrangement of the housing seats on a display and/or in an automatic configuration and guiding process of a visual signalling device or an automatic depositing device of the samples.

In a further aspect thereof, the invention further relates to a process, according to any one of the appended process claims, or the further aspects indicated herein, wherein the step of reading by the electronic memorising device is performed before a step of arranging a plurality of samples of material on the support body.

In a further aspect thereof, the invention further relates to a process, according to any one of the appended process claims, or the further aspects indicated herein, wherein a step of memorising on an electronic memorising device is performed before the step of arranging a plurality of material samples and before a step of reading by the electronic memorising device.

In a further aspect thereof, the invention further relates to a process, according to any one of the appended process claims, or the further aspects indicated herein, wherein the step of memorising on an electronic memorising device is performed in a different place from the place in which the step of positioning a plurality of material samples and/or the step of reading by the electronic memorising device are performed.

In a further aspect thereof, the invention further relates to a process, according to any one of the appended process claims, or the further aspects indicated herein, wherein the step of memorising on an electronic memorising device is performed substantially contemporaneously (or contextually) with the step of arranging a plurality of samples of material on the support body.

In a further aspect thereof, the invention further relates to a process, according to any one of the appended process claims, or the further aspects indicated herein, wherein the step of reading the plurality of data and/or the identifying datum by the electronic memorising device is not included.

In a further aspect thereof, the invention further relates to a process, according to any one of the appended process claims, or the further aspects indicated herein, wherein the step of memorising on an electronic memorising device is performed after the step of arranging a plurality of samples of material on the support body.

In a further aspect thereof, the invention further relates to a process, according to any one of the appended process claims, or the further aspects indicated herein, wherein the step of cancelling the plurality of data from the electronic memorising device and/or updating the data and/or replacing the data with a corresponding plurality of updated or modified data and/or the step of saving the plurality of data, before cancelling from the memorising device of the support device, on an information system or an external historical database.

In a further aspect thereof, the invention further relates to a process, according to any one of the appended process claims, or the further aspects indicated herein, further comprising the step of projecting at least a light signal on the support body, during the step of positioning a plurality of material samples, at the effective position or housing seat in which each material sample is arranged, in order to guide the positioning or for indicating the positioning visibly.

In a further aspect thereof, the invention further relates to a process, according to any one of the appended process claims, or the further aspects indicated herein, further comprising the step of registering images or photographs at least of a part of the support body during the step of arranging a plurality of samples of material, and conserving and/or verifying the images to confirm a real arrangement of the plurality of samples of material on the support body.

In a further aspect thereof, the invention further relates to a process, according to any one of the appended process claims, or the further aspects indicated herein, further comprising the step of memorising on the memorising device the results of the analyses performed on the samples deposited on the support device, in corresponding combination with the plurality of data on the samples or on the arrangement thereof on the support body.

In a further aspect thereof, the invention further relates to a process, according to any one of the appended process claims, or the further aspects indicated herein, wherein the step of reading from the electronic memorising device and/or the step of memorising on the electronic memorising device are performed substantially contemporaneously (or contextually) with the step of arranging the plurality of samples and/or in a protected environment in a laminar flow hood.

In a further aspect thereof, the invention further relates to a process, according to any one of the appended process claims, or the further aspects indicated herein, further comprising the step of automatically positioning, via an automatic positioning device, the samples in the plurality of housing seats of the support device, guided by the processor and/or commanded by the software program.

In a further aspect thereof, the invention further relates to a process, according to any one of the appended process claims, or the further aspects indicated herein, wherein the electronic memorising device comprises at least a TAG or a registrable RFID transponder, provided at least which an electronic memory chip and an RFID antenna and/or wherein the memorising device is a TAG or RFID transponder of a passive type.

There now follows, by way of non-limiting example, a detailed description of one or more preferred embodiments of the invention, wherein.

An apparatus 1 is described for processing samples of biological, microbiological and/or chemical material, in accordance with some embodiments of the invention.

The apparatus 1 comprises, first of all, a support device 2 for samples of biological, microbiological and/or chemical material. By "biological" material, reference is also made to material of biological origin.

The device 2 comprises at least a transportable support body 3, provided with a plurality of housing seats 4 each destined to receive at least a sample of biological, microbiological and/or chemical material.

The support device 2 further comprises at least an electronic memorising device 5, registrable and suitable for storing a plurality of information relating at least to the samples of material and to the specific position of each of the material samples on the support body 3, at each of the housing seats 4. The memorising device 5 is constrained to the support body 3 in such a way as to be transportable together with the support body 3.

The plurality of information stored on the memorising device 5 can comprise, for each sample or analyte, at least a datum concerning the nature or type of the sample and/or the origin of the sample, and at least a datum concerning the specific position of the sample on the support body 3 of the support device 2 or the specific housing seats 4 in which the sample is arranged on the support body 3.

The memorising device 5 can be further provided with at least a univocal and sole identifying datum of the support device 2, such as a unique identifying serial number of the support, for example stored in an area or portion of memory dedicated to factory data and not rewritable, in a substantially permanent and not erasable way. In this case the support device 2 can do without a conventional identification label or bar code, as it can be uniquely identified automatically by the apparatus 1 using the said identifying datum.

Alternatively, the support device 2 can be provided with an identifying label or bar code and thus be uniquely identified by the apparatus 1 by means of a univocal and sole identifying datum obtainable from the equipment by reading the bar code or by manually entering the datum. The memorising device 5 can be further provided with one or more items of data relating to the technical characteristics of the support device, chosen from among the following: the type of support, the type of surface of the support, the number of housing seats on the support, the arrangement of the housing seats on the support, the coordinates of the housing seats on the support, the presence or absence of culture media on the support. The data are for example stored in a memorising portion dedicated to factory information and not rewritable.

The memorising device 5 can be cancellable and rewritable a plurality of times to allow selectively to erase and rewrite the above-mentioned plurality of data, after the completion of each series of analysis.

Preferably the univocal and sole identifying datum is stored permanently and therefore is not cancellable. The memorising device 5 may comprise at least a TAG or an registrable RFID transponder, provided with at least an electronic memorising chip and an RFID antenna.

The memorising device 5 can be a TAG or RFID transponder of a passive type, which is powered by an external power source when reading or writing data. In a variant, the memorising device 5 can include a non-RFID type electronic memory card.

In a further variant, the memorising device 5 can be of another type suitable for the purpose. The memorising device 5 can be integrated in the support body 3, for example, internally of the support body 3.

The support body 3 can have a flat, continuous surface that is non-porous at and in proximity of the point where the memorising device 5 is fitted on the support body 3. These characteristics are especially important in a case where the support device 2 has to operate under vacuum, for example in a case where an MALDI TOF analysis plate is present.

Figure 3:
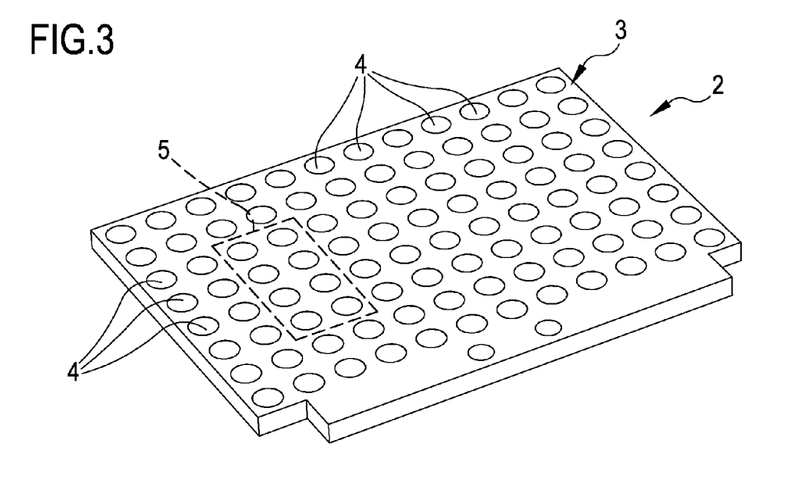
FIG. 3 is a support device according to a second embodiment of the present invention.
Figure 4:
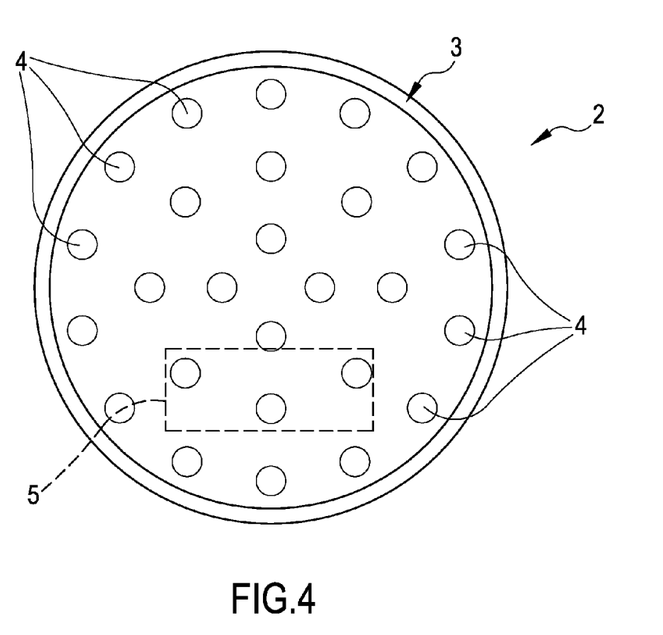
FIG. 4 is a support device according to a third embodiment of the present invention.

In a preferred embodiment, illustrated in FIGS. 3 and 4, the support body 3 can be realized in a single piece. The memorising device 5 can be housed in the support body 3.

Figure 1:
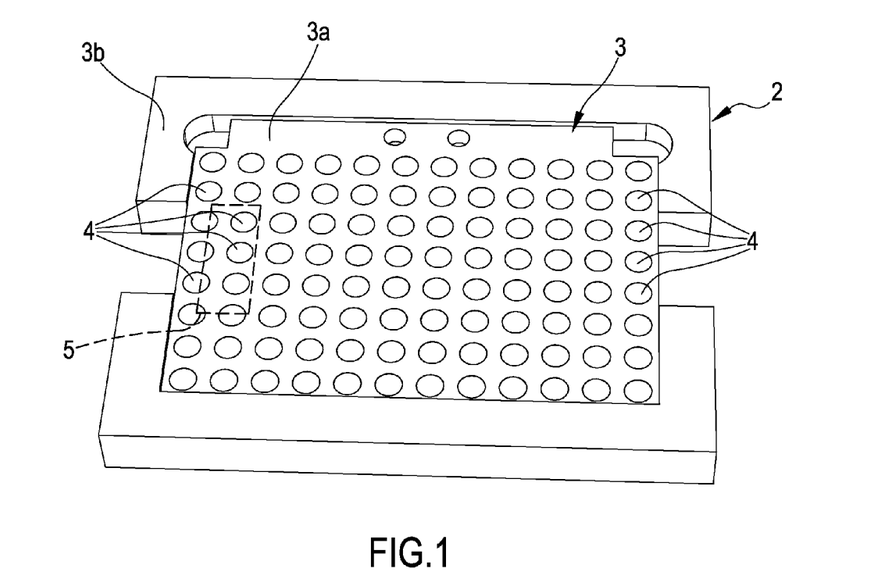
FIG. 1 is a support device of a first embodiment of the present invention.
Figure 2:
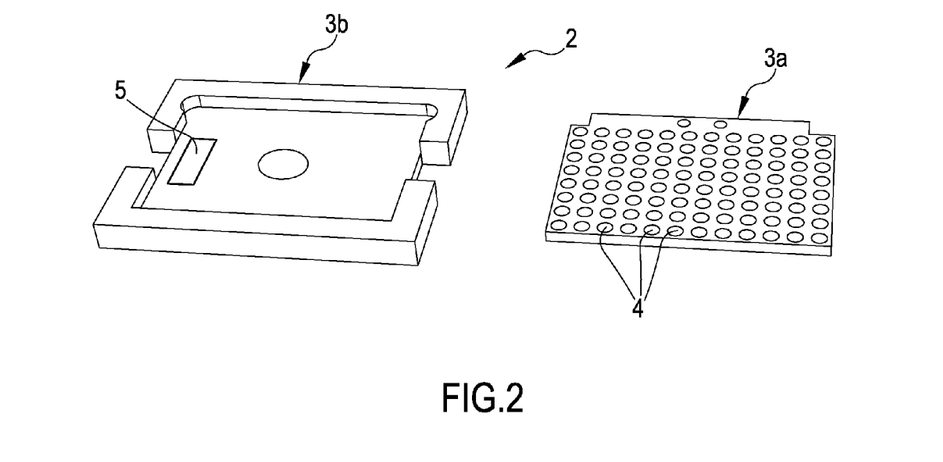
FIG. 2 is the device of FIG. 1, partially exploded.

In another embodiment, illustrated in FIGS. 1 and 2, the support body 3 can comprise a first half-body 3a in which the housing seats 4 are defined, and a second half-body 3b in which the memorising device 5 is accommodated, the first and second half-bodies 3a, 3b being mutually constrained such as to define the support device 2. The memorising device 5 in this case is preferably housed at an internal portion of the second half-body 3b, facing towards the first half-body 3a, so as to remain enclosed between the two half-bodies in the entire support body 3.

The support body 3 can be a type that can be reused a plurality of times. In this case the support body 3 can be made for example of a metal material, e.g. steel. In a variant, the support body 3 can be of a disposable type. In this case the support body 3 can be made for example of plastic material. The first half-body 3a can also be made of a first material, e.g. metal, and that the second half-body 3b can be made of a second material, e.g. plastic.

The support device 2 can exhibit a matrix of housing seats 4. These seats 4 can be positioned in an ordered arrangement on the support body 3, for example in a plurality of rows and columns (as shown in FIGS. 1-3), in a honeycomb, in concentric circumferences (as in FIG. 4), or another ordered arrangement. The housing seats 4 can be defined and delimited in a finite number on the support body 3, as in the above figures, and can also be numbered or otherwise indicated.

The housing seats 4 may consist of wells formed in the support body 3 for housing of samples of biological, microbiological and/or chemical material. The housing seats 4 can also not be detectably defined on the support body 3, and can be defined solely following the positioning of the samples on the support body 3 or by means of a light signal, as described below. In this case the housing seats 4 are characterized and defined solely by the deposition coordinates of the samples themselves.

Figure 5:
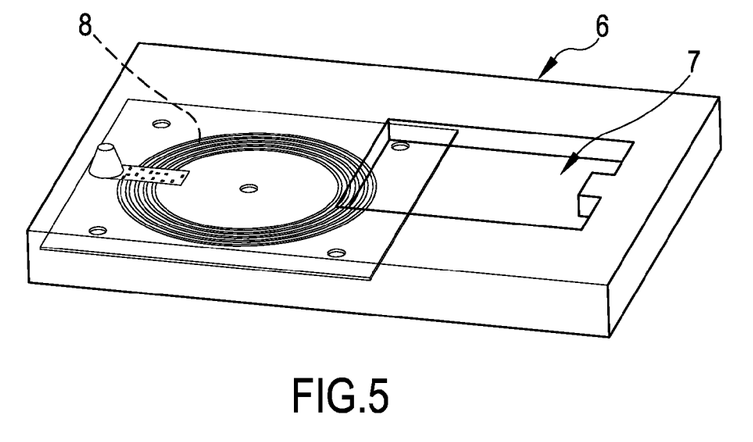
FIG. 5 is an embodiment of an interface device with a support device according to one of FIGS. 1 to 4.
Figure 6:
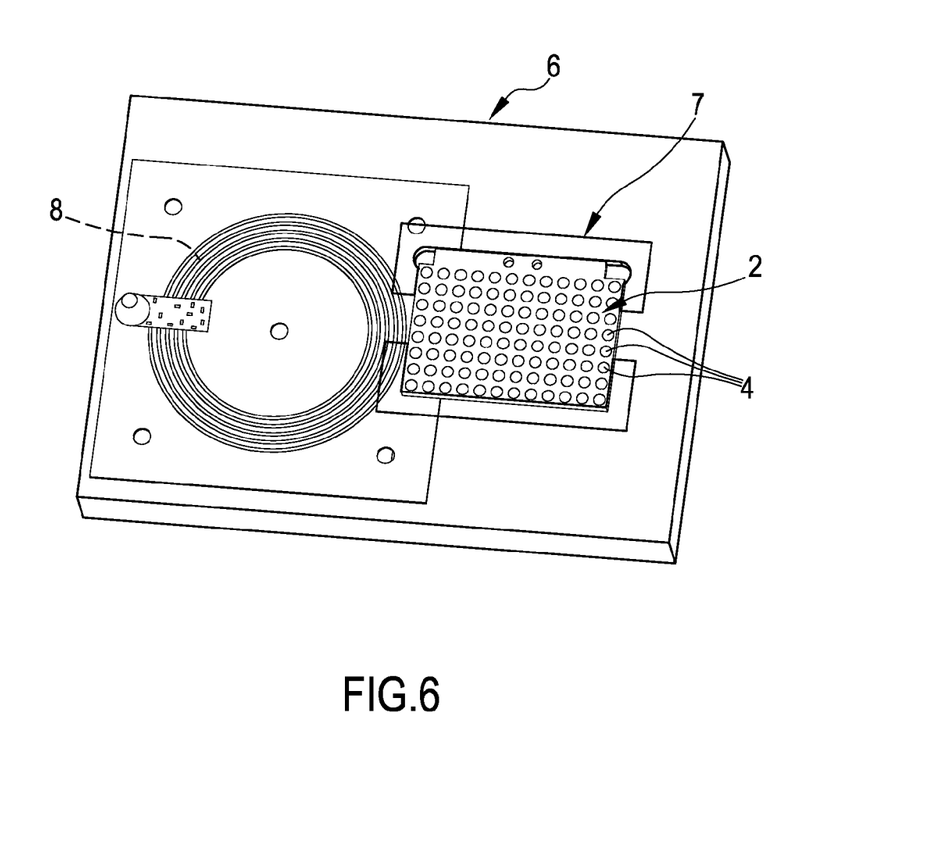
FIG. 6 is the support device of FIG. 1 mounted on the interface device of FIG. 5.

The support body 3 can be a support plate, such as a Petri dish or a MALDI TOF plate for mass spectrometry. The support body 3 can be provided with at least a culture medium for microorganisms at least in some of the housing seats 4. As shown in FIG. 5, the apparatus 1 further comprises at least an interface device 6 with the support device 2. The interface device 6 comprises at least one support portion 7 suitable for housing the support device 2 and at least a transmission device 8 destined to read and edit the contents of the electronic memorising device 5 of the support device 2. FIG. 6 shows the support device 2 mounted on the interface device 6.

Figure 9:
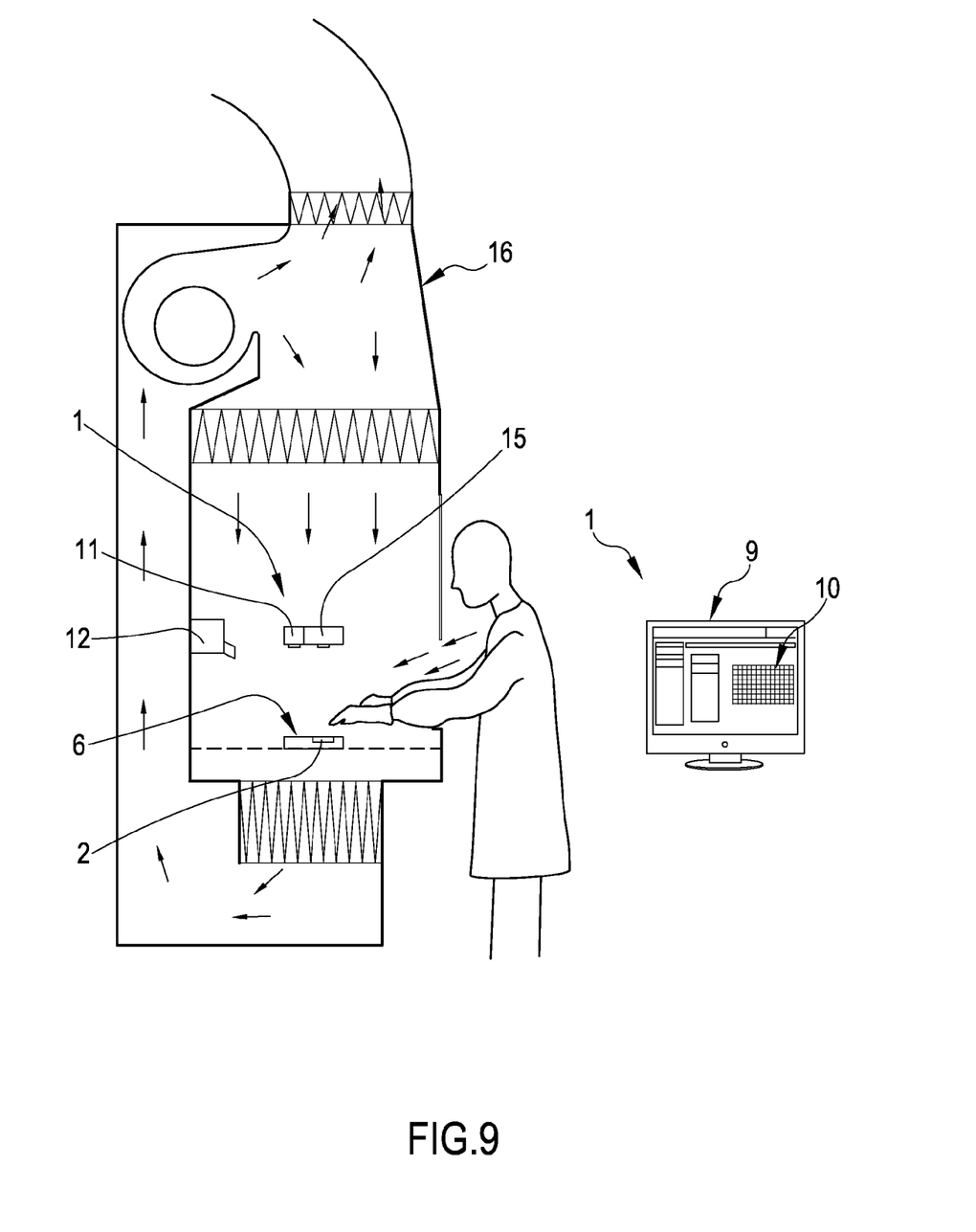
FIG. 9 is a schematic illustration of a laminar flow hood provided with an apparatus according to an embodiment of the present invention.

The transmission device 8 may comprise at least a RFID transceiver provided with at least an antenna for reading and/or writing the contents of the electronic memorising device 5, of the RFID type. In a case in which the memorising device 5 is of the passive type, the interface device 6 will provide, in a known way, the energy required for its operation for reading and writing. As can be seen in FIG. 9, the support device 2 for interface device 6 with the support device 2 can be adapted and configured to be arranged and to operate in a protected environment under a laminar flow hood 16 (shown schematically in FIG. 9, with the flow of forced air indicated) and such as to interface one another in the protected environment.

The apparatus 1 can further comprise at least a processor 9 operatively connected to the interface device 6 and at least a software program 10 memorised and operating on the processor 9 and destined to manage the operation of the interface device 6. The software 10 can control the execution of at least some of the steps of the procedure, as will be described later.

Figure 7:
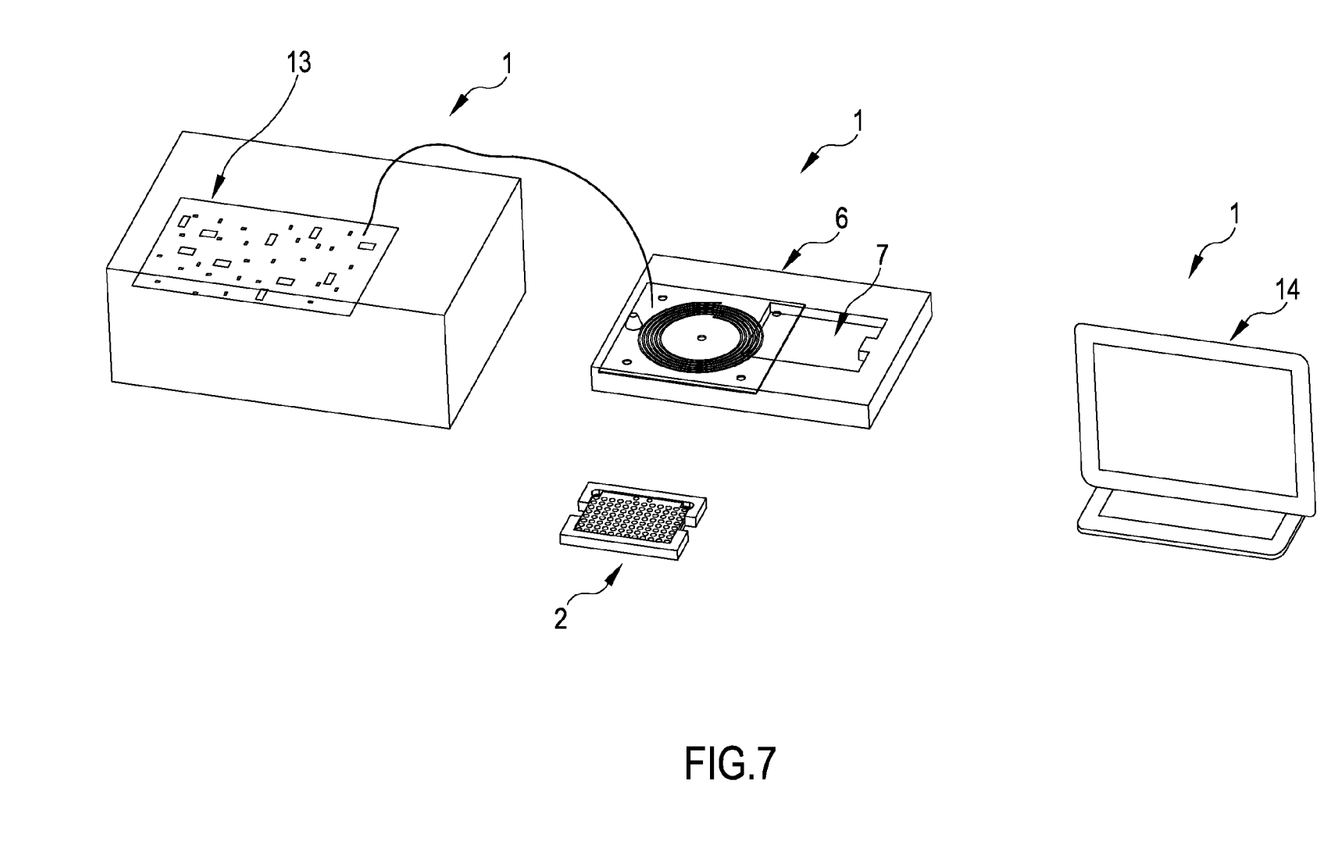
FIG. 7 illustrates some components of an apparatus according to an embodiment of the present invention.

The interface device 6 can comprise a support portion 7 destined to house a plurality of different types of support devices 2. As shown in the embodiment of FIG. 7, the processor 9 can for example include a control card 13 operatively connected to the interface device 6, and a touch-screen panel 14 operatively connected to the control card 13 and destined to command functioning. The software 10, or a portion of additional software, can be installed and operated on the touch-screen panel.

The processor 9 can further comprise, in addition to or alternatively to the touch-screen panel, a common PC or other type of processor 9 or computer system interfaced with the control card 13 and on which the software 10 operates.

The apparatus 1 can further comprise at least a visual signalling device 11, destined to emit a light signal on the support body 3 of the support device 2 housed on the interface device 6, such as to visually indicate an actual position or housing seat 4 in which a sample of material is positioned, such as to guide the positioning of the sample material or to define and delimit the plurality of housing seats on the support body (essentially drawing a light reticulation defining the locations) and/or to visibly indicate the positioning. The visual signalling device 11 may for example be a laser pointer device, automated and motorized, which can be controlled by the software 10 of the processor 9 such as to progressively indicate the various positions (in terms of abscissas and ordinates) or housing, deposition or inoculating seats of the samples on the support body 3.

Figure 10:
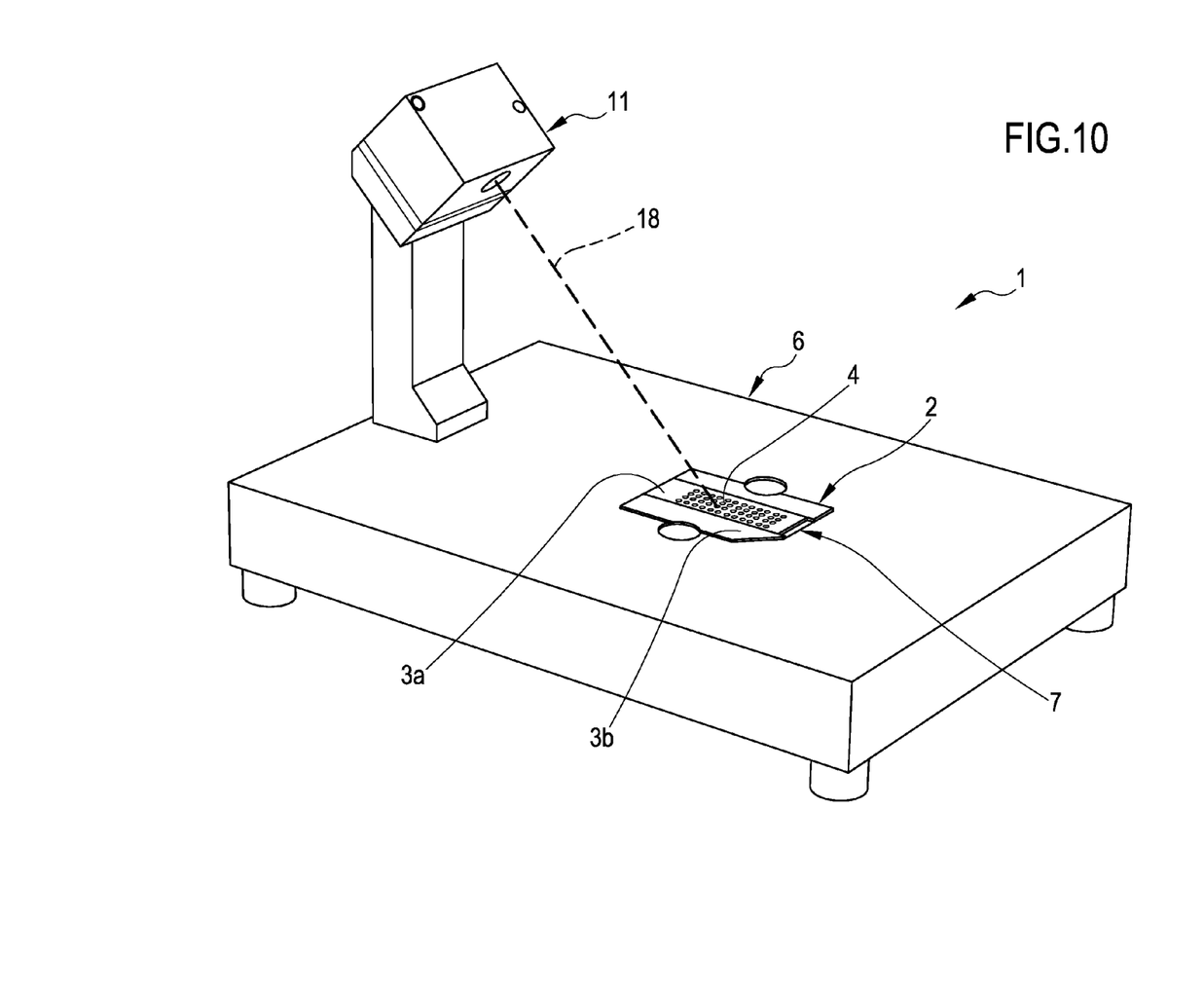
FIG. 10 is an alternative embodiment of some components illustrated in FIG. 7.

In the alternative embodiment illustrated in FIG. 10, the control card 13 is accommodated in the body of the interface device 6, together with the transmitting device 8 and the support portion 7 (not shown for the sake of simplicity and as it is housed inside the body). Further, in this embodiment, the visual signalling device 11 is also mounted on the body of the interface device 6, which as shown in FIG. 10 is destined to emit for example a laser beam 18 indicating a respective housing seat 4 in the sample is deposited. Otherwise this alternative solution is alike the one previously described.

The apparatus 1 can further comprise at least a device 12 for recording images or photographs for recording images at least of the support body 3 during the positioning of a plurality of material samples, and then recording the depositing step of the sample and/or the presence of the above-mentioned light signal at the housing seats 4 where the deposition of the material takes place. The recording device can be connected to the processor 9 so as to transfer these images to the computer 9, which is destined to store and/or verify these images to confirm the actual arrangement of the plurality of samples of material on the support body 3.

The apparatus 1 can further comprise a device 15 for automatically depositing samples (shown schematically in FIG. 9), operatively connected to the processor 9 and/or controlled by the software 10 for inoculating or guidedly depositing the samples in the plurality of housing seats 4 of the support device 2.

The invention further relates to the use of a support device 2 and/or an interface device 6 and/or an apparatus 1 of the type described above for the depositing, the inoculating, transporting and/or the analysis of samples of biological, microbiological and/or chemical material in diagnostic, medical, analytical, chemical, environmental, food and/or industrial fields.

The invention further relates to a method for the treatment of samples of biological, microbiological and/or chemical material, comprising at least a step of positioning a plurality of samples of biological, microbiological and/or chemical material on a corresponding plurality of housing seats 4 of a transportable support body 3 of a support device 2. The arrangement of the samples can be done in a known manner, e.g. by inoculating microbiological samples or by depositing of biological samples diluted in a liquid.

The process can further comprise the step of storing, on a memorising electronic device 5 constrained to the support body 3 such as to be transportable together with the support body 3, a plurality of data relating at least to the samples of biological, microbiological and/or chemical material and also relating to the specific positioning of each of them on the support body 3, in the housing seats 4.

The process can further comprise the step of reading, by the electronic memorising device 5 constrained to the support body 3 such as to be transportable together with the support body 3, at least the plurality of data relating at least to the samples of biological, microbiological and/or chemical material and to the specific arrangement to be performed for each of them on the support body 3, in the housing seats 4.

The process can further comprise the step of reading, by the electronic memorising device 5 constrained to the support body 3 such as to be transportable together with the support body 3, at least a univocal and sole identifying datum of the support device 2, in order to identify with certainty, and automatically, each specific support device 2. It is possible, during the afore-mentioned step of reading by the electronic memorising device 5, that only the univocal and sole identifying datum of the support device 2 will be read, for example in a case where the memorising of the plurality of data relating to the samples and the arrangement thereof takes place during the depositing of the samples themselves. The step of reading by the electronic memorising device 5 is preferably carried out before the step of positioning a plurality of samples of material on the support body 3, both in order possibly to read the identifying datum and possibly to read the data relating to the arrangement of the samples to be performed.

The process might not include any step of reading by the device 5 for storing the plurality of electronic information and/or the identifying datum during the depositing of the sample, in the case where the support device 2 can be identified by other means and the work pattern is established simultaneously with the depositing of the samples.

The step of storing on the electronic memorising device 5 can be performed before the step of placing a plurality of samples of material and before the step of reading by the electronic memorising device 5. The step of storing on the electronic memorising device can also be carried out in a different place to the one where the step of depositing a plurality of samples of material takes place and/or the step of reading by the electronic memorising device 5 is performed. This happens for example in the case in which a first processing system is used to plan the arrangement of the samples on the support device 2, registering work patterns on the memorising device 5 of the support 2, and then transferring the support device 2 to a second processing system, at which the reading of the memorising device 5 is performed such as to enable identification of the support device 2 itself (which could also be performed by means of conventional bar codes or other known methods) and the reading of the work pattern with the depositing of samples which are to be positioned on the support body 3.

Alternatively, the step of storing on the electronic memorising device 5 can be carried out substantially simultaneously with the step of arranging the plurality of samples of material on the support body 3, for example in the case where the working pattern with the positioning of the samples on the support body 3 is not imported from another system, but it is established directly just before or during the depositing of the samples, recording it on the memorising device 5 in order to enable subsequent reading, e.g. in seats 4 in combination with the results of the analysis or what is recorded on the memorising device 5. The step of reading from the electronic memorising device 5 and/or the step of storing on the electronic memorising device 5 can be carried out substantially simultaneously with the step of arranging the plurality of samples and/or in a protected environment under a laminar flow hood 16.

Figure 8:
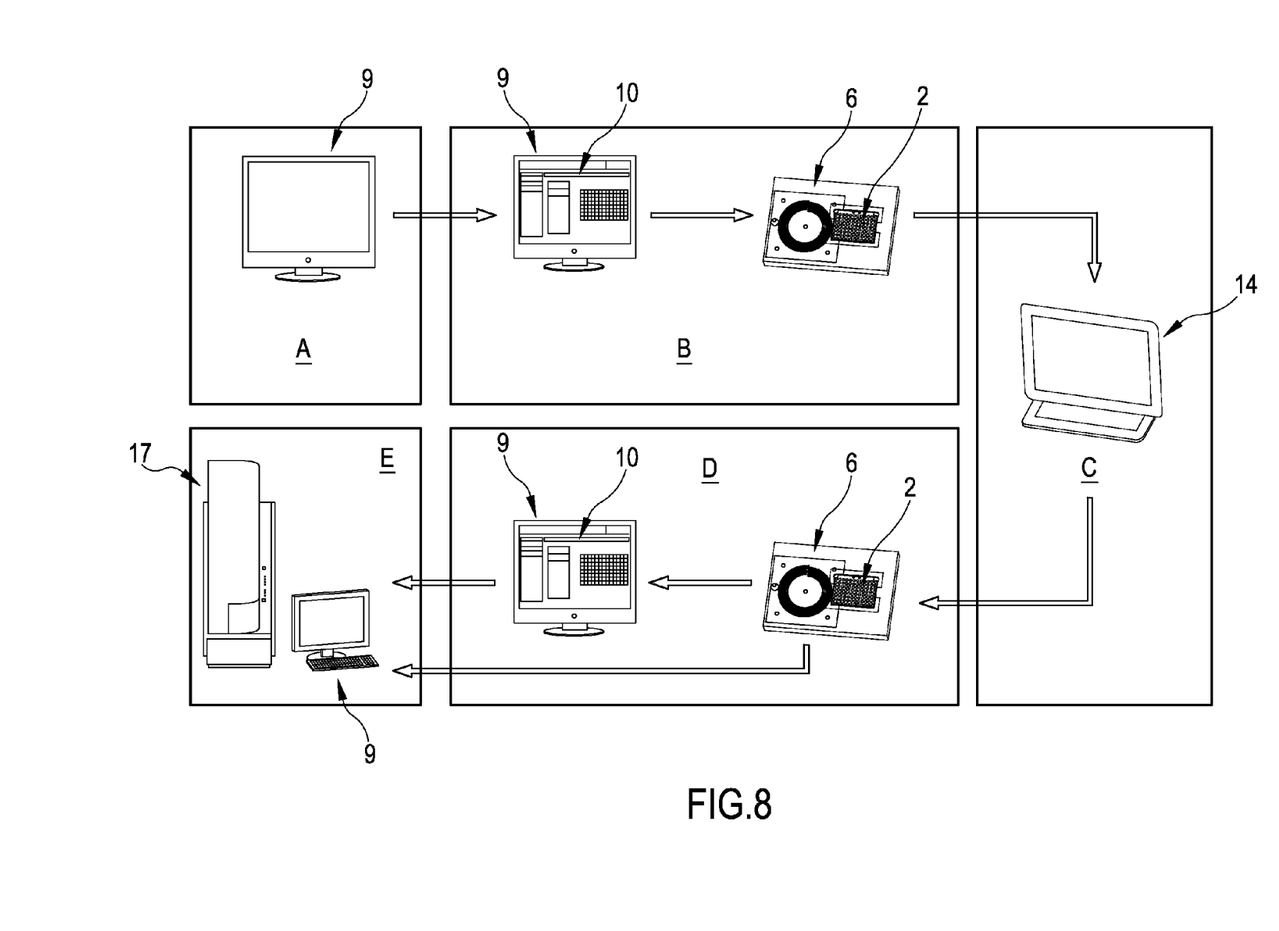
FIG. 8 is a diagram illustrating some steps of a process according to an embodiment of the present invention.

In a variant, the step of storing on the electronic memorising device 5 can also be carried out after the step of placing a plurality of material samples on the support body 3. FIG. 8 shows a flow diagram of an embodiment of the procedure, in which the work pattern is initially designed in a computer system laboratory (step A), and then is realized with work management software 10 and is stored on the memorising device 5 of the support device 2 for the work (step B). At this point the samples are deposited (step C) in a guided step in accordance with the established work pattern. Subsequently, in another place, the prepared support device 2 and its contents are recognised (step D) and the support device 2 is subjected to further analysis (step E), such as a MALDI-TOF analysis in a relevant spectrometric analysis apparatus 17, with automatic matching of the results to the respective samples by the computer system. The method may further comprise the step of deleting the plurality of information from the electronic memorising device 5 and/or updating and/or replacing them with a corresponding plurality of updated or modified information, for example to enable re-use of the support device 2. This information, before its removal from the memorising device 5, 9, can be registered on the processor 9 or on another data system such as to enable entering in a historical database and re-use for performing further studies or compiling further statistics.

The process can further comprise the step of projecting at least a light signal on the support body 3, during the step of positioning a plurality of material samples, onto the actual position or housing seats 4 in which each sample of material is disposed, such to guide the positioning or to clearly display the positioning.

The process can further comprise the step of recording images or photographs of at least part of the support body 3 of during the step of arranging a plurality of material samples, and to maintain and/or verify these images such as to confirm the actual arrangement of the plurality of material samples on the support body 3.

The process can further comprise the step of automatically depositing the samples, by means of the above-mentioned automatic depositing device 15, in the plurality of housing seats 4 of the support device 2, guided by the processor 9 and/or controlled by the software 10. In substance, the process can be realized in different ways, including for example the following: 1) a work pattern can be prepared on a first computer system for the positioning of the samples, which pattern can be registered on the memorising device 5 of the support device 2, by means of an interface device 6, and then the support device 2 can be transferred to the laboratory where the depositing of the samples takes place. In the laboratory, the support device 2 is coupled with a local interface device 6 which enables identification of the support device 2 and reading of the work pattern, which is then carried out by depositing, possibly automatically, the samples on the device. The depositing can be guided by a light signal that indicates the locations 4 where the sample is to be positioned, and images can be taken to confirm the correct deposition of each sample. The support device 2 thus prepared can then be transferred to the place where further analysis of the samples is to be performed, with the possibility of newly re-reading the work pattern stored on the device and automatically matching the results of the analysis to the plurality of data on the samples, possibly also storing them on the memorising device 5, or on the local computer system; 2) the work pattern can be determined directly from the software 10 present in the laboratory in which the depositing of the samples takes place, and in this case the identification of the support device 2 is performed first (via the bar code or by means of the univocal datum of the memorising device 5), after which it proceeds to perform the depositing of the samples and, simultaneously or subsequently, the memorising of the data regarding the samples and their location on the memorising device 5. Then the same operations as in the first option are performed. 3) In a variant, a substantially free positioning of the samples on the support device 2 can be performed, collecting and recording on the data storage device 5 the information relating to the samples and their positioning while performing the depositing, or immediately thereafter.

The present invention enables one or more of the following advantages to be obtained. First, the invention overcomes the drawbacks encountered in the prior art. The invention also obviates or at least significantly reduces the risk of human error in the performing of procedures for the analysis and/or the calculating of the results.

The invention also provides a high degree of reliability and repeatability of results, and provides an apparatus and method for the treatment of samples or analytes that are extremely flexible and adaptable to different operating requirements and to different types of analysis.

The invention also enables simplification of the data treatment processes resulting from analysis of the samples, and also enables portability of information between different and unrelated computer systems.

The invention also provides complete traceability of historical information related to the analyses performed and the devices and samples, and leads to research results and statistics that further increase the quality of the analyses performed, and security of the environments.

The invention also provides significantly increased sample process analysis safety, as well as the security of patients and the various parties involved in the analysis.

Lastly, the invention is simple and economical to implement.

The invention claimed is:

1. An apparatus for treating samples of biological, microbiological and/or chemical material, comprising at least:
   a support device (2) for samples of biological, microbiological and/or chemical material, the support device (2) having at least a transportable support body (3) provided with a plurality of housing seats (4) suitable for each receiving at least a sample of biological, microbiological and/or chemical material, wherein said support device (2) further comprises an electronic memorizing device (5), registrable and suitable for memorizing a plurality of data relating at least to said samples of material and to the specific position of each of said samples of material on said support body (3), in correspondence of each of said housing seats (4), said electronic memorizing device (5) being constrained to said support body (3) for being transportable together with said support body (3);
   an interface device (6) for interfacing with the support device (2), wherein said interface device comprises at least a support portion (7) suitable for housing said support device (2), wherein said interface device (6) comprises at least a transmitting device (8) suitable for reading and/or modifying the contents of the electronic memorizing device (5) of said support device (2);
   a processor (9);
   at least a software program (10) memorized on said processor (9); and
   at least a visual signaling device (11), operatively connected to said processor (9) and controlled by said software program (10) and suitable for emitting a light signal on said support body (3) of said support device (2) housed on said interface device (6), for visually indicating an effective position or housing seat (4) in which a sample of material is arranged, for guiding the positioning of the sampling of material or for visually indicating such positioning or for defining and delimiting said plurality of housing seats on said support body (3);
   wherein the transmitting device (8) is accommodated in a body of the interface device (6).

2. The apparatus of claim 1, wherein said processor (9) is operatively connected to said interface device (6).

3. The apparatus of claim 1, wherein the memorizing device (5) is cancellable and rewritable a plurality of times for enabling selective cancellation and rewriting of said plurality of data and/or wherein said memorizing device (5) is further provided with at least a univocal and sole identifying datum of said support device (2) and/or of at least a datum relating to a technical characteristic of the support device (2), selected at least from the following: a type of support device (2), a type of surface of the support device (2), a number of housing seats of the support device (2), a positioning of the housing seats on the support device (2), arrangement of the housing seats on the support device (2), the coordinates of the housing seats on the support device (2), a presence or not of culture media on the support device (2) and/or in that the memorizing device (5) comprises at least a portion of non-rewritable memory in which the at least a univocal and sole identifying datum of said support device (2) and/or the at least a datum relating to a technical characteristic of the support device (2) are permanently stored.

4. The apparatus of claim 3, wherein said apparatus is predisposed and configured for acquiring said univocal and sole identifying datum of the support device (2) by means of a manual entering of the datum itself into said processor (9) or by reading a bar code.

5. The apparatus of claim 1 wherein said memorizing device (5) comprises at least a TAG or a registrable RFID transponder, provided at least with an electronic chip for memorizing and with an RFID antenna and/or wherein the memorizing device (5) is a TAG or an RFID transponder of a passive type and/or wherein said memorizing device (5) is integrated in the support body (3) and/or integrated internally of said support body (3) and/or wherein the support body (3) exhibits a flat, continuous and non-porous surface in correspondence and in proximity of the mounting point of said memorizing device (5) on said support body (3).

6. The apparatus of claim 5, wherein the transmitting device (8) comprises at least an RFID transceiver provided with at least an antenna for reading and/or writing the contents of said RFID-type electronic memorizing device (5).

7. The apparatus of claim 1, further comprising at least a registration device (12) of images or photographs for recording images at least of said support body (3) during the positioning of a plurality of samples of material and/or wherein the registration device (12) is connected to said processor (9) in such a way as to transfer said images to said processor (9), which is apt to conserve and/or verify said images to confirm a real arrangement of said plurality of samples of material on said support body (3).

8. The apparatus of claim 1, wherein at least the support device (2) and the interface device (6) and/or the processor (9) and/or the same apparatus for treating samples of biological, microbiological and/or chemical material, are apt and configured for being arranged and for operating in a protected environment under laminar flow hood (16) and for interfacing reciprocally in such protected environment.

9. The apparatus of claim 1, further comprising an automatic depositing device of the samples, operatively connected to said processor (9) and/or commanded by said software program for inoculating or depositing in guided manner the samples in correspondence of a plurality of housing seats (4) of the support device (2).

10. The apparatus of claim 1, wherein said visual signaling device (11) is a laser pointer device and/or wherein said visual signaling device (11) is suitable for emitting a laser ray (18) indicating a respective housing seating (4) in which the sample is deposited.

11. The apparatus of claim 1, wherein said visual signaling device (11) is automated and motorized.

12. The apparatus of claim 1, wherein said visual signaling device (11) is commanded by said software program (10) of said processor (9) for progressively indicating the positions or housing seats (4), depositing seats or inoculation seats of said samples on said support body (3) and/or wherein said software (10) is configured and operatively active for controlling the functioning of said visual signaling device (11).

13. The apparatus of claim 1, wherein said visual signaling device (11) is apt to emit said light signal on said support body (3) for selectively indicating said effective position or housing seat (4) and/or wherein said visual signaling device (11) is controlled by said software program (10) for indicating a single positioning seat at a time or wherein said signaling device (11) is controlled by said software program (10) for simultaneously indicating at least two of said housing seats (4).

14. The apparatus of claim 1, wherein said software program (10) is suitable for using a univocal and sole identifying datum of the support device (2) and/or one or more items of data relating to technical characteristics of the support device (2) at least for further visualizing a representation of the support device (2) and of the relative arrangement of said housing seats (4) on a display.

15. The apparatus of claim 1, wherein said software program (10) is suitable for using a univocal and sole identifying datum of the support device (2) and/or one or more items of data relating to technical characteristics of the support device (2) at least for actuating an automatic configuration and/or a guiding procedure of said visual signaling device (11).

16. The apparatus of claim 1, wherein said processor (9) comprises a control board (13) operatively connected to said interface device (6), and/or comprises a touch-screen panel (14) operatively connected to the control board (13) and suitable for commanding functioning thereof and/or wherein said software program (10), or a portion thereof of additional software, is installed and operates on the touch-screen panel (14) and/or wherein the processor (9) further comprises, additionally or alternatively to the touch-screen panel (14), a PC or other type of processor (9) or information system interfaced with the control board (13) and on which the software program (10) operates and/or wherein said control board (13) is housed internally of the interface device (6), together with the transmitting device (8) and the support portion (7).

17. The apparatus of claim 1, wherein the visual signaling device (11) is also mounted to the body of the interface device (6).

18. The apparatus of claim 1, wherein the support portion (7) is adaptable for housing a plurality of different types of support devices (2).

19. A process for treating samples of biological, microbiological and/or chemical material, comprising at least a step of arranging a plurality of samples of biological, microbiological and/or chemical material on a corresponding plurality of housing seats (4) of a transportable support body (3) of a support device (2), further comprising a step of projecting onto the support body (3) at least a light signal (18), during the step of arranging said plurality of material samples, in correspondence of the effective position or housing seat or seats (4) wherein each sample of material is arranged, such as to guide the positioning or to indicate the positioning visibly;

further comprising at least one from among the following steps:
  memorizing, on an electronic memorizing device (5) constrained to said support body (3) for being transportable together with said support body (3), a plurality of data relating at least to said samples of biological, microbiological and/or chemical material and to a specific positioning of said samples on the support body (3), in correspondence of said housing seats (4); and/or
  reading, from said electronic memorizing device (5) constrained to the support body (3) for being transportable together with said support body (3), at least a univocal and sole identifying datum of said support device (2) and/or at least a datum relating to a technical characteristic of the support device (2) and/or a plurality of data relating at least to said samples of biological, microbiological and/or chemical material and to a specific positioning to be performed for each thereof on said support body (3), in correspondence of said housing seats (4);

wherein memorizing and/or reading are performed by a transmitting device (8) of an interface device (6), wherein the transmitting device (8) is suitable for reading and/or modifying the contents of the electronic memorizing device (5) of said support device (2); wherein the transmitting device (8) is accommodated in a body of the interface device (6).

20. The process of claim 19, wherein said light signal (18) is projected onto the support body (3) selectively in correspondence of said effective position or housing seat (4) or seats (4) and/or further comprising a step of progressively indicating the positions or housing seats (4), deposition seats or inoculation seats of said samples on said support body (3), by means of said light signal (18), indicating a single positioning seat at a time or simultaneously indicating at least two of said positioning seats.

21. The process of claim 19, further comprising a step of using a univocal and sole identifying datum of the support device (2) and/or one or more data relating to technical characteristics of the support device in a software program (10) suitable for managing the functioning of an interface device with said support device (2).

22. The process of claim 19, further comprising a step of using a univocal and sole identifying datum of the support device (2) and/or one or more data relating to technical characteristics of the support device (2) in a software program (10) destined to visualize, on a display, a representation of the support device (2) and the relative arrangement of the housing seats (4).

23. The process of claim 19, further comprising at least a step of using a univocal and sole identifying datum of the support device (2) and/or one or more data relating to technical characteristics of the support device (2) in a process of automatic configuration and guide of said visual signaling device.

24. The process of claim 19, wherein the electronic memorizing device (5) comprises at least a TAG or a registrable RFID transponder, provided at least with an electronic memory chip and an RFID antenna and/or wherein the memorizing device (5) is a TAG or RFID transponder of a passive type.

25. The process of claim 19, wherein during said step of reading from the electronic memorizing device (5), constrained to the support body (3) for being transportable together with the support body (3), reading is made of only a univocal and sole identifying datum of the support device (2) and/or one or more items of data relating to technical characteristics of the support device (2), selected from among the following: the type of support device (2), the type of surface of the support device (2), the number of housing seats (4) of the support device (2), the arrangement of the housing seats (4) on the support device (2), the coordinates of the housing seats (4) on the support device (2), the presence or not of culture media on the support device (2) and/or wherein the step of reading from the electronic memorizing device (5) is performed before a step of arranging a plurality of material samples on the support body (3).

26. The process of claim 19 wherein a step of memorizing on an electronic memorizing device (5) is performed before the step of arranging a plurality of material samples and before the step of reading from the electronic memorizing device (5) and/or wherein the step of memorizing on an electronic memorizing device (5) is performed in a different place to the place in which the step of arranging a plurality of material samples is performed and/or the step of reading from the electronic memorizing device (5) is performed, and/or wherein the step of memorizing on an electronic memorizing device (5) is performed substantially contextually with the step of arranging a plurality of material samples on the support body (3) and/or wherein the step of memorizing on an electronic memorizing device (5) is performed after the step of arranging a plurality of material samples on the support body (3).

27. The process of claim 19, wherein the step of reading said plurality of data and/or the identifying datum from the electronic memorizing device (5) is not performed.

28. The process of claim 19, further comprising the step of cancelling the plurality of data from the electronic memorizing device (5) and/or updating the data and/or replacing the data with a corresponding plurality of updated or modified data and/or the step of saving said plurality of data, before cancelling from the memorizing device (5) of the support device (2), on an information system or an external historical database.

29. The process of claim 19, wherein said step of projecting at least a light signal (18) on the support body (3) is performed by means of a visual signaling device (11) and/or by means of a visual signaling device (11) of a laser type.

30. The process of claim 19, further comprising a step of registering images or photographs at least of a part of the support body (3) during the step of arranging a plurality of samples of material, and conserving and/or verifying the images to confirm a real arrangement of the plurality of samples of material on the support body (3).

31. The process of claim 19, further comprising the step of memorizing on the electronic memorizing device (5) and/or on said processor (9) the results of analyses performed on the samples deposited on the support device (2), in corresponding matching with the aforesaid plurality of data on the samples or on the arrangement thereof on the support body (3).

32. The process of claim 19, wherein the step of reading from the electronic memorizing device (5) and/or the step of memorizing on the electronic memorizing device (5) are performed substantially contextually with the step of arranging the plurality of samples and/or in a protected environment in a laminar flow hood (16).

33. The process of claim 19, further comprising a step of using a univocal and sole identifying datum of the support device (2) and/or one or more items of data relating to technical characteristics of the support device (2) in an automatic configuration and guide process and of an automatic depositing device of the samples and/or further comprising the step of automatically depositing the samples, by means of an automatic depositing device, in correspondence of the plurality of housing seats (4) of the support device (2), guided by the processor (9) and/or commanded by the software program (10).

34. The process of claim 33, comprising the step of obtaining said univocal and sole identifying datum of the support device (2) by means of reading a bar code or by manually entering the datum acquired from, for example, an identifying datum of the support device (2).

35. An apparatus for treating samples of biological, microbiological and/or chemical material, comprising at least:

a support device (2) for samples of biological, microbiological and/or chemical material, the support device (2) having at least a transportable support body (3) provided with a plurality of housing seats (4) suitable for each receiving at least a sample of biological, microbiological and/or chemical material;

an interface device (6) for interfacing with the support device (2), wherein said interface device comprises at least a support portion (7) suitable for housing said support device (2); a processor (9);

at least a software program (10) memorized on said processor (9);

at least a visual signaling device (11), operatively connected to said processor (9) and controlled by said software program (10) and suitable for emitting a light signal on said support body (3) of said support device (2) housed on said interface device (6), for visually indicating an effective position or housing seat (4) in which a sample of material is arranged, for guiding the positioning of the sampling of material or for visually indicating such positioning or for defining and delimiting said plurality of housing seats on said support body (3);

at least a registration device (12) of images or photographs for recording images at least of said support body (3) during the positioning of a plurality of samples of material and wherein the registration device (12) is connected to said processor (9) in such a way as to transfer said images to said processor (9), which is apt to conserve and/or verify said images to confirm a real arrangement of said plurality of samples of material on said support body (3).

* * * * *